United States Patent
Williams (10) Patent No.: US 9,301,757 B2
(45) Date of Patent: Apr. 5, 2016

(54) SURGICAL FASTENER APPLYING APPARATUS INCLUDING FLUID-ACTIVATED FIRING MECHANISM

(71) Applicant: Covidien LP, Mansfield, MA (US)

(72) Inventor: Justin Williams, Naugatuck, CT (US)

(73) Assignee: Covidien LP, Mansfield, MA (US)

( * ) Notice: Subject to any disclaimer, the term of this patent is extended or adjusted under 35 U.S.C. 154(b) by 521 days.

(21) Appl. No.: 13/915,891

(22) Filed: Jun. 12, 2013

(65) Prior Publication Data

US 2014/0027492 A1 Jan. 30, 2014

Related U.S. Application Data

(60) Provisional application No. 61/676,408, filed on Jul. 27, 2012.

(51) Int. Cl.
| | |
|---|---|
| *A61B 17/068* | (2006.01) |
| *A61B 17/072* | (2006.01) |
| *A61B 17/00* | (2006.01) |
| *A61B 17/29* | (2006.01) |

(52) U.S. Cl.
CPC ........... *A61B 17/068* (2013.01); *A61B 17/0686* (2013.01); *A61B 17/07207* (2013.01); *A61B 2017/00398* (2013.01); *A61B 2017/00539* (2013.01); *A61B 2017/00544* (2013.01); *A61B 2017/00734* (2013.01); *A61B 2017/07278* (2013.01); *A61B 2017/2923* (2013.01); *A61B 2017/2927* (2013.01)

(58) Field of Classification Search
CPC .................................................... A61B 17/068
USPC ................... 227/176.1, 175.2, 175.1
See application file for complete search history.

(56) References Cited

U.S. PATENT DOCUMENTS

| | | | |
|---|---|---|---|
| 4,331,277 A | 5/1982 | Green | |
| 4,485,817 A | 12/1984 | Swiggett | |

(Continued)

FOREIGN PATENT DOCUMENTS

EP 2100562 A2 9/2009

OTHER PUBLICATIONS

Extended European Search Report issued in corresponding application No. EP13178240.1 on Oct. 1, 2015.

(Continued)

*Primary Examiner* — Andrew M Tecco
*Assistant Examiner* — Praachi M Pathak (57) ABSTRACT

A surgical fastener applying apparatus includes an end effector assembly having an anvil assembly and a cartridge assembly. The anvil assembly and/or the cartridge assembly is movable relative to the other between open and closed positions. The cartridge assembly is configured to retain a plurality of surgical fasteners therein. A fluid-actuated drive assembly including a distal piston member is configured to oscillate between proximal and distal positions. The distal piston member includes a base and a rack extending distally from the base and slidably disposed within the cartridge assembly. A drive beam is configured for translation through the cartridge assembly to eject the surgical fasteners from the cartridge assembly. A pawl assembly couples the drive beam to the rack such that the drive beam is incrementally advanced along the rack and through the cartridge assembly as the distal piston member oscillates between the proximal position and the distal position.

11 Claims, 7 Drawing Sheets

(56) References Cited

U.S. PATENT DOCUMENTS

| | | | |
|---|---|---|---|
| 4,488,523 A | 12/1984 | Shichman | |
| 4,962,877 A | 10/1990 | Hervas | |
| 5,312,023 A | 5/1994 | Green et al. | |
| 5,326,013 A | 7/1994 | Green et al. | |
| 5,364,001 A | 11/1994 | Bryan | |
| 5,395,030 A | 3/1995 | Kuramoto et al. | |
| 5,411,508 A | 5/1995 | Bessler et al. | |
| 5,487,499 A | 1/1996 | Sorrentino et al. | |
| 5,575,799 A | 11/1996 | Bolanos et al. | |
| 5,782,397 A | 7/1998 | Koukline | |
| 6,250,532 B1 | 6/2001 | Green et al. | |
| 6,830,174 B2 | 12/2004 | Hillstead et al. | |
| 7,246,734 B2 | 7/2007 | Shelton, IV | |
| 7,431,189 B2 | 10/2008 | Shelton, IV et al. | |
| 7,441,684 B2 | 10/2008 | Shelton, IV et al. | |
| 7,448,525 B2 | 11/2008 | Shelton, IV et al. | |
| 7,559,450 B2 * | 7/2009 | Wales | A61B 17/00234 227/175.1 |
| 7,670,334 B2 | 3/2010 | Hueil et al. | |
| 7,740,159 B2 | 6/2010 | Shelton, IV et al. | |
| 8,453,914 B2 * | 6/2013 | Laurent | A61B 17/068 227/179.1 |
| 8,740,036 B2 * | 6/2014 | Williams | A61B 17/07207 227/177.1 |
| 2006/0151567 A1 | 7/2006 | Roy | |
| 2006/0201990 A1 * | 9/2006 | Mastri | A61B 17/0684 227/176.1 |
| 2007/0102473 A1 | 5/2007 | Shelton et al. | |
| 2007/0102474 A1 | 5/2007 | Shelton et al. | |
| 2008/0029570 A1 | 2/2008 | Shelton et al. | |
| 2008/0029573 A1 | 2/2008 | Shelton et al. | |
| 2008/0029574 A1 | 2/2008 | Shelton et al. | |
| 2008/0029575 A1 | 2/2008 | Shelton et al. | |
| 2010/0252610 A1 | 10/2010 | Viola | |
| 2012/0181322 A1 | 7/2012 | Whitman et al. | |

OTHER PUBLICATIONS

Pneumatic cylinder, Wikipedia, the free encyclopedia, Jul. 20, 2012, XP055214272, Retrieved from the Internet: URL:https://en.wikipedia.org/w/index.php?title=Pneumatic_cylinder&oldid=503238052#Types, [retrieved on Sep. 17, 2015].

* cited by examiner

SURGICAL FASTENER APPLYING APPARATUS INCLUDING FLUID-ACTIVATED FIRING MECHANISM

CROSS-REFERENCE TO RELATED APPLICATIONS

This application claims the benefit of and priority to U.S. Provisional Patent Application No. 61/676,408, filed Jul. 27, 2012, the entire disclosure of which is incorporated by reference herein

BACKGROUND

1. Technical Field

The present disclosure relates to surgical fastener applying apparatus and, more particularly, to a fluid-activated, e.g., pneumatic or hydraulic, surgical fastener applying apparatus for clamping, fastening, and cutting tissue.

2. Background of Related Art

Surgical fastener applying apparatus, wherein tissue is first grasped or clamped between opposing jaw structures and then joined by means of surgical fasteners, are well known. In some such apparatus, a knife is provided to cut tissue that has been joined by the fasteners. The fasteners are typically in the form of surgical staples, although other surgical fasteners may also be utilized, such as, for example, clips or two part polymeric surgical fasteners.

Surgical fastener applying apparatus, as mentioned above, typically include two opposed jaw structures that are used to capture or clamp tissue therebetween. Typically, one of the jaw structures carries a cartridge assembly which houses a plurality of fasteners arranged in at least two lateral rows, while the other jaw structure includes an anvil which defines a surface for forming the fastener legs as the fasteners are driven from the cartridge assembly. Generally, the fastener formation process is affected by the interaction between one or more longitudinally moving camming members and a series of individual pushers. As the camming members travel longitudinally through the cartridge assembly, the individual pushers are biased upwardly into a backspan of the fasteners supported within the cartridge assembly to sequentially eject the fasteners from the cartridge. Where a knife is provided, the knife follows the camming members and travels between the fastener rows to cut tissue between the rows of formed fasteners.

SUMMARY

In accordance with the present disclosure, a surgical fastener applying apparatus is provided. The surgical fastener applying apparatus includes an end effector assembly, a fluid-actuated drive assembly, a drive beam, and a pawl assembly. The end effector assembly includes an anvil assembly and a cartridge assembly. One or both of the anvil assembly and the cartridge assembly is movable relative to the other between an open position and a closed position for grasping tissue therebetween. The cartridge assembly is configured to retain a plurality of surgical fasteners therein. The fluid-actuated drive assembly includes a distal piston member configured to oscillate between a proximal position and a distal position. The distal piston member includes a base and a rack extending proximally from the base. The rack is slidably disposed within the cartridge assembly. The drive beam is configured for translation through the cartridge assembly to eject the plurality of surgical fasteners from the cartridge assembly. The pawl assembly couples the drive beam to the rack such that the drive beam is incrementally advanced along the rack and through the cartridge assembly as the distal piston member oscillates between the proximal position and the distal position.

In embodiments, the fluid-actuated drive assembly includes a distal piston assembly including a piston housing. The distal piston member is disposed within the piston housing and is configured such that fluid pressure within the piston housing urges the distal piston member to move from the proximal position to the distal position.

In embodiments, the distal piston member is biased towards the proximal position such that, in the absence of fluid pressure within the piston housing, the distal piston member is returned from the distal position to the proximal position.

In embodiments, the drive assembly further includes a proximal piston assembly and an elongated tube coupling the proximal piston assembly and the distal piston member. The elongated tube is substantially filled with a fluid such that oscillation of the proximal piston assembly between first and second positions effects oscillation of distal piston member between the proximal and distal positions.

In embodiments, the surgical fastener applying apparatus further includes a motor assembly coupled to the proximal piston assembly and configured to drive the proximal piston assembly to oscillate between the first and second positions.

In embodiments, the motor assembly includes an axle and a drive member eccentrically mounted about the axle. The motor is configured to rotate the axle such that the drive member is rotated by the axle to drive the proximal piston assembly to oscillate between the first and second positions.

In embodiments, the drive beam is further configured to engage the anvil assembly and the cartridge assembly upon distal translation of the drive beam to move the end effector assembly from the open position to the closed position.

In embodiments, the pawl assembly is configured to engage the drive beam to the rack upon movement of the distal piston member from the proximal position to the distal position. The pawl assembly is further configured to disengage the drive beam from the rack upon movement of the distal piston member from the distal position back to the proximal position.

In embodiments, the pawl assembly includes a pawl pivotably coupled to the drive beam. The pawl includes a free end configured to engage a tooth of the rack upon movement of the distal piston member from the proximal position to the distal position and configured to slid about teeth of the rack upon movement of the distal piston member from the distal position back to the proximal position.

In embodiments, the surgical fastener applying apparatus further includes a retraction assembly coupled to the drive beam and the pawl assembly. The retraction assembly is selectively actuatable for translating the drive beam proximally through the cartridge assembly.

In embodiments, the retraction assembly includes a retraction cord coupled to the drive beam and the pawl assembly at a first end thereof. The retraction cord has a retraction knob disposed at a second end thereof.

BRIEF DESCRIPTION OF THE DRAWINGS

The above and other aspects, features, and advantages of the present disclosure will become more apparent in light of the following detailed description when taken in conjunction with the accompanying drawings, wherein.

DETAILED DESCRIPTION

Embodiments of the presently disclosed fluid-activated, e.g., pneumatic or hydraulic, surgical fastener applying apparatus for clamping, fastening, and cutting tissue are described in detail with reference to the drawings wherein like reference numerals identify similar or identical structural elements in each of the several views. As used herein, as is traditional, the term "proximal" refers to the end of the apparatus or component thereof that is closer to the user, while the term distal refers to the end of the apparatus or component thereof that is further from the user.

With reference to FIGS. 1-11, an exemplary surgical fastener applying apparatus 10 provided in accordance with the present disclosure is shown. Surgical fastener applying apparatus 10 is configured as a handheld, endoscopic surgical fastener applying apparatus 10 and generally includes a motorized handle assembly 100 having an elongated member 200 extending distally therefrom and an end effector assembly 300 operably disposed at a distal end of elongated member 200. However, other suitable surgical fastener applying apparatus, e.g., open surgical fastener applying apparatus, manually-powered surgical fastener applying apparatus, etc., are also contemplated for use in accordance with the present disclosure.

Referring to FIGS. 1-4, motorized handle assembly 100 of surgical fastener applying apparatus 10 includes a housing 102, one or more actuator buttons 104a for activating end effector assembly 300, e.g., to initiate a clamping, fastening, and/or cutting operation, one or more actuator buttons 104b for articulating end effector assembly 300 relative to elongated member 200 (see FIG. 2), and a retraction knob 196 for resetting end effector assembly 300 after a clamping, fastening, and/or cutting operation. Housing 102 houses the internal working components of motorized handle assembly 100 and includes an ergonomic handle portion 108, a battery compartment 110, a cylindrical body portion 112, and a distal nose portion 114 extending distally from cylindrical body portion 112. Handle portion 108 is configured to facilitate the operative grasping of housing 102 by the user. A motor assembly 120 and the proximal portion 142 of a drive assembly 140, as will be described in greater detail below, are disposed within distal nose portion 114 of housing 102. Battery compartment 110 is configured to releasably receive a battery pack 116 for providing power to motor assembly 120 and/or articulatable joint assembly 310 of end effector assembly 300. Actuator button 104a is electrically coupled between battery pack 116 and motor assembly 110 for selectively activating motor assembly 110 to initiate a clamping, fastening, and cutting operation. Motor assembly 120, drive assembly 140, elongated member 200, and end effector assembly 300 will be described in greater detail below. Further discussion of the construction, features, and operation of a suitable motorized handle assembly configured for use with surgical fastener applying apparatus 10 can be found in U.S. patent application Ser. No. 12/622,827, filed on Nov. 20, 2009, and entitled "Surgical Console and Hand-held Surgical Device," the entire contents of which are hereby incorporated by reference herein.

Figure 1:
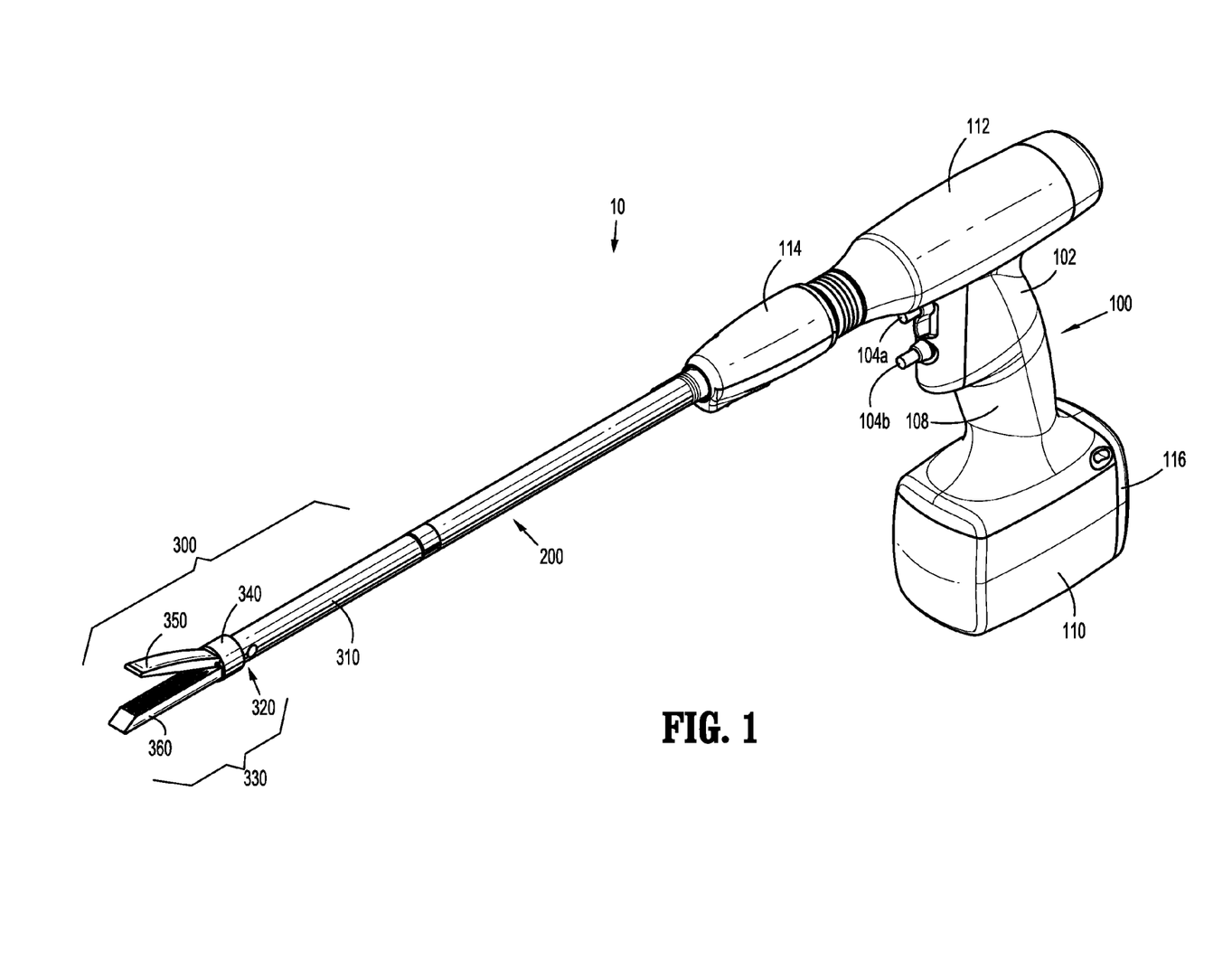
FIG. 1 is a front, perspective view of an endoscopic, handheld surgical fastener applying apparatus provided in accordance with the present disclosure.
Figure 2:
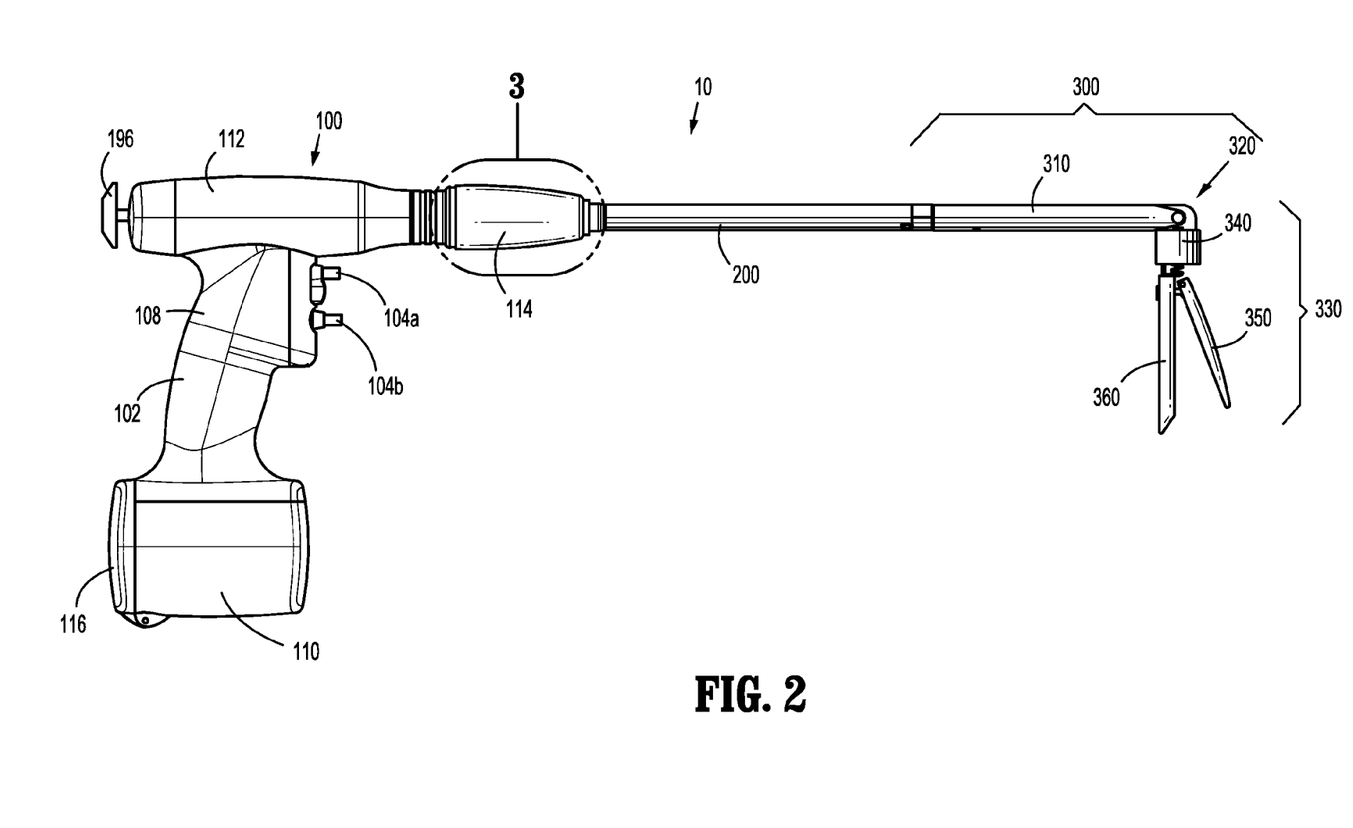
FIG. 2 is side view of the surgical fastener applying apparatus of FIG. 1, shown with the end effector assembly disposed in an articulated position.
Figure 3:
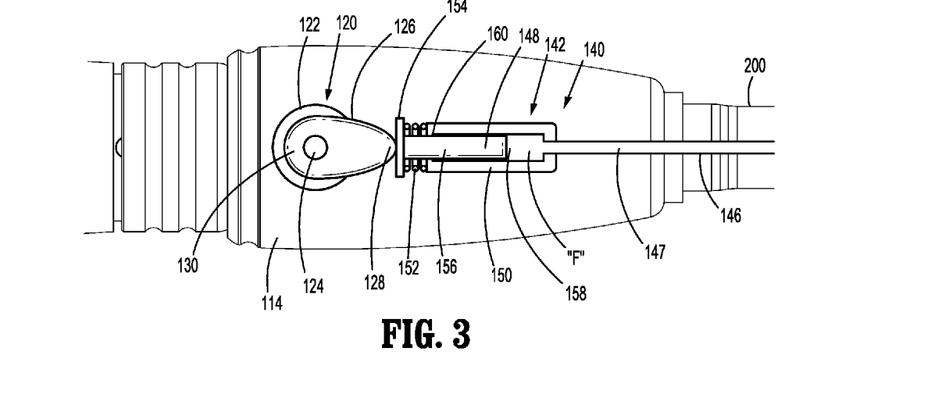
FIG. 3 is an enlarged, schematic illustration of the area of detail indicated as "3" in FIG. 2, wherein the motor assembly is disposed in a first position.
Figure 4:
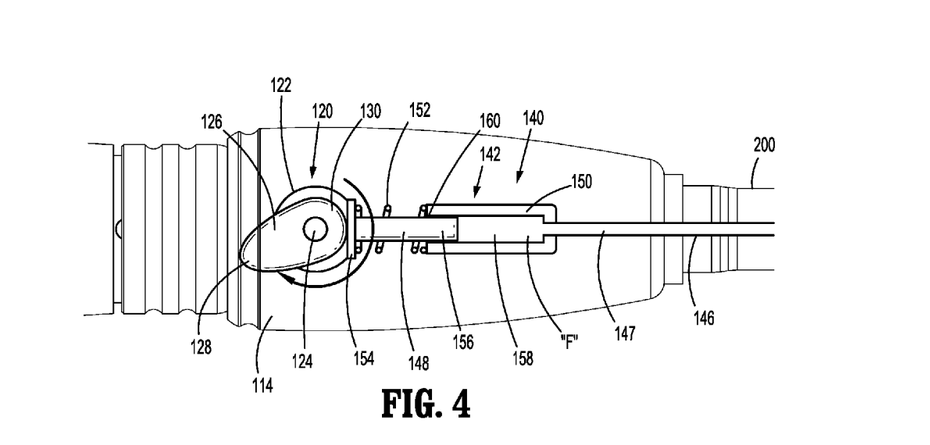
FIG. 4 is an enlarged, schematic illustration of the area of detail indicated as "3" in FIG. 2, wherein the motor assembly is disposed in a second position.

Continuing with reference to FIGS. 1-4, and to FIGS. 3 and 4 in particular, motor assembly 120 includes a motor 122 configured to drive rotation of an axle 124. Motor 122 is coupled to battery pack 116 and actuator button 104a such that, upon actuation of actuator button 104a, power is supplied from battery pack 116 to motor 122 to drive axle 124. A generally oval-shaped drive member 126 is eccentrically mounted about drive axle 124. That is, drive member 126 is mounted about drive axle 124 such that a first end 128 thereof extends radially-outwardly from axle 124 a greater distance than the second end 130 thereof. As will be described below, piston 148 of drive assembly 140 is biased proximally into abutment with drive member 126 of motor assembly 120 such that rotation of the eccentrically mounted drive member 126 by axle 124 urges piston 148 distally against its bias and allows piston 148 to return proximally under bias upon each revolution of drive member 126.

Drive assembly 140 includes a proximal portion 142 disposed within distal nose portion 114 of housing 102 distally adjacent motor assembly 120, a distal portion 144 disposed within proximal housing 340 of distal tool assembly 330 of end effector assembly 300 (see FIG. 5), and an elongated fluid tube 146 extending between the proximal and distal portion 142, 144 (FIG. 5), respectively, of drive assembly 140. Proximal portion 142 of drive assembly 140 includes a piston 148, a piston-receiving member 150, e.g., a cylinder, and a biasing member 152 interdisposed between piston 148 and piston-receiving member 150. Piston 148 includes a head 154 and a body portion 156 that is slidably disposed within piston-receiving member 150 in sealing relation therewith. Biasing member 152 biases head 154 of piston 148 proximally such that body portion 156 of piston 148 is biased outwardly from piston-receiving member 150, although body portion 156 of piston 148 is inhibited from fully backing out of piston-receiving member 150. Piston-receiving member 150 defines an internal cavity 158 that communicates at its distal end with elongated fluid tube 146. Piston-receiving member 150 further includes a proximal aperture 160 configured, as mentioned above, to slidingly receive body portion 156 of piston 148 in sealing relation therewith. Internal cavity 158 of piston-receiving member 150, internal passageway 147 of elongated fluid tube 146, and internal cavity 342 (FIG. 5) of proximal housing 340 (FIG. 5) of distal portion 144 (FIG. 5) of drive assembly 140 cooperate to define a cavity that is substantially filled with a pre-determined volume of fluid "F," e.g., gas or liquid, for, as will be described in detail below, pneumatically or hydraulically actuating end effector assembly 300 (FIG. 5) to clamp, fasten, and/or cut tissue.

With reference to FIGS. 1 and 2, elongated member 200 extends distally from distal nose portion 114 of motorized handle assembly 100 and interconnects motorized handle assembly 100 and end effector assembly 300. More specifically, elongated member 200 may be configured to releasably engage end effector assembly 300 at the distal end thereof (as shown), e.g., via bayonet coupling, snap-fit, or other suitable engagement mechanism, or may have end effector assembly 300 permanently affixed to the distal end thereof. Elongated member 200 defines a generally tubular configuration for housing elongated fluid tube 146 of drive assembly 140, retraction cord 192 (FIGS. 6 and 7) of retraction assembly 190, and/or any of the other components interconnected between motorized handle assembly 100 and end effector assembly 300, e.g., leads (not shown) for electrically coupling actuator button 104b to articulating joint assembly 320.

Figure 5:
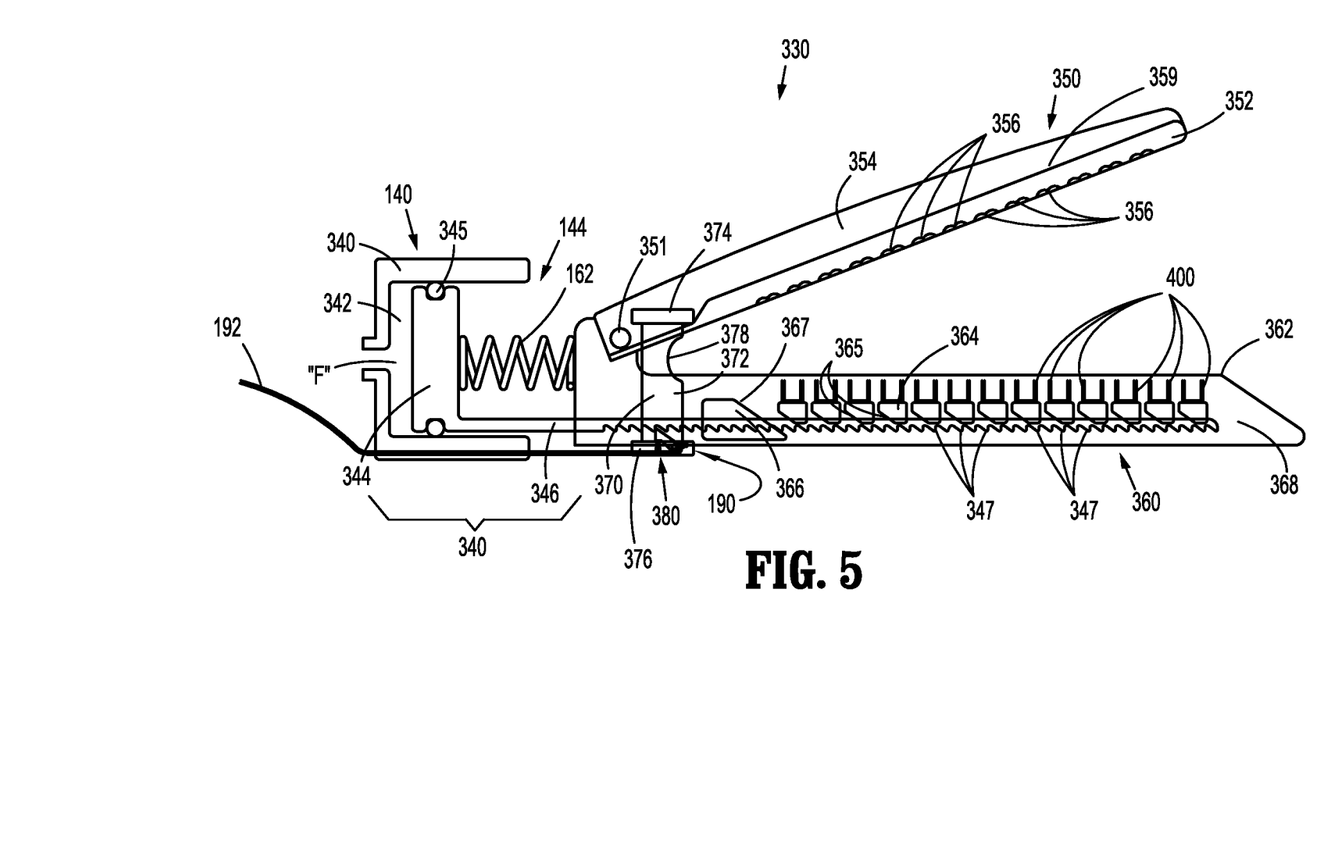
FIG. 5 is a longitudinal, cross-sectional view of the end effector assembly of the surgical fastener applying apparatus of FIG. 1, wherein the end effector assembly is disposed in an initial, unclamped, and unfired condition.

Continuing with reference to FIGS. 1-2, and with additional reference to FIG. 5, as mentioned above, end effector assembly 300 is disposed at the distal end of elongated member 200 and may be releasably engagable with the distal end of elongated member 200. End effector assembly 300 includes a proximal shaft portion 310, an articulatable joint assembly 320, and a distal tool assembly 330. Proximal shaft portion 310 is configured to releasably engage the distal end of elongated member 200. Alternatively, in embodiments where end effector assembly 300 is permanently affixed to the distal end of elongated member 200, proximal shaft portion 310 may be integral with or otherwise engaged to elongated member 200. It is also contemplated that, in any of the embodiments disclosed herein, the staple cartridge can be a removable and replaceable assembly.

Articulatable joint assembly 320 of end effector assembly 300 is disposed between proximal shaft portion 310 and distal tool assembly 330. Articulatable joint 320 is operably coupled to actuator button 104b of motorized handle assembly 100 such that, upon manipulation of actuator button 104b, end effector assembly 300 may be articulated relative to elongated member 200 in a desired direction. Alternatively or additionally, articulatable joint assembly 320 may be articulated manually, or by any other suitable mechanical, electrical, or electromechanical mechanism extending between motorized handle assembly 100 and articulatable joint assembly 320. Further, articulatable joint assembly 320 may include any suitable articulation mechanism configured to permit articulation of end effector assembly 300 relative to elongated member 200, such as, for example, gears, wires, cables, linkages, and combinations thereof.

Figure 10:
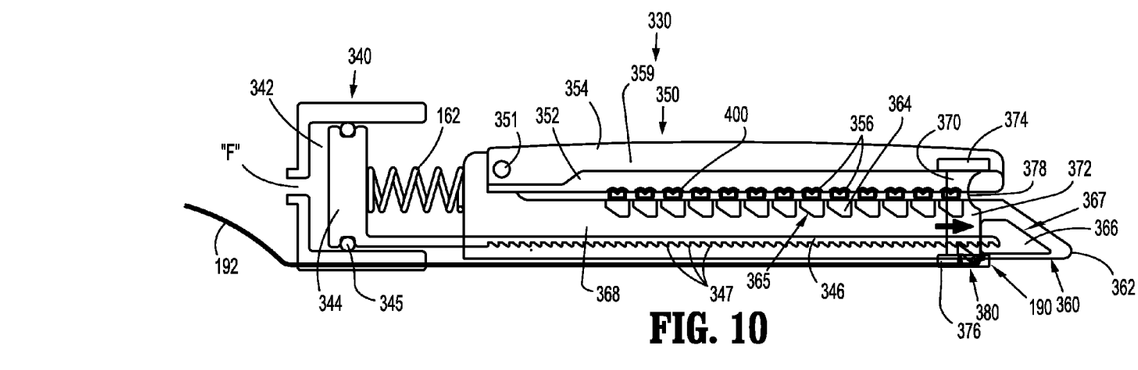
FIG. 10 is a longitudinal, cross-sectional view of the end effector assembly of FIG. 5, wherein the end effector assembly is disposed in a clamped and fully fired condition.
Figure 11:
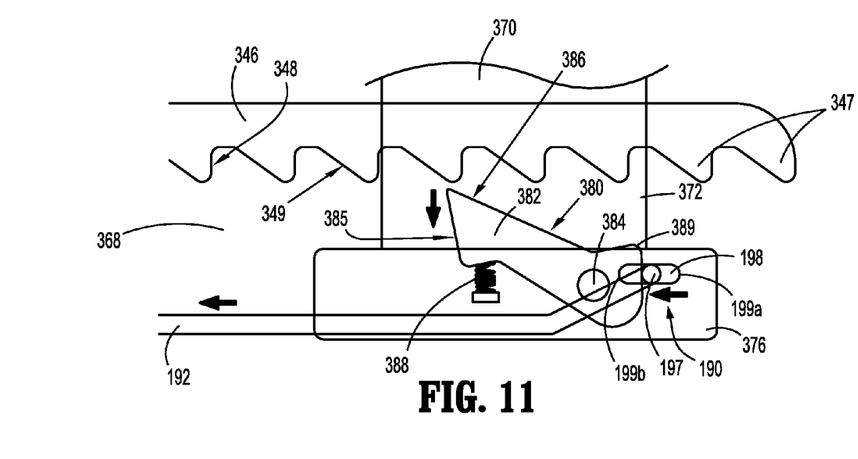
FIG. 11 is a greatly enlarged, longitudinal, cross-sectional view of the drive beam and rack and pawl system of FIG. 5 during refraction of the drive beam.

Referring to FIG. 5 in particular, distal tool assembly 330 of end effector assembly 300 includes a proximal housing 340, an anvil assembly 350, and a cartridge assembly 360. Proximal housing 340 houses distal portion 144 of drive assembly 140. Anvil assembly 350 is pivotably coupled to proximal housing 340 and cartridge assembly 360 such that anvil assembly 350 may be pivoted relative to cartridge assembly 360 between an open position, wherein anvil assembly 350 and cartridge assembly 360 are spaced-apart from one another (FIG. 5), and a closed position, wherein anvil assembly 350 is disposed in close approximation with cartridge assembly 360 to clamp tissue therebetween (FIG. 10). Cartridge assembly 360 is mounted, integrally formed, or otherwise fixedly engaged to proximal housing 340 and extends distally therefrom. However, it is also envisioned that this configuration be reversed, e.g., wherein anvil assembly 350 is mounted to proximal housing 340 and cartridge assembly 360 is pivotable relative to anvil assembly 350 and proximal housing 340. Alternatively, distal tool assembly 330 may define a bilateral configuration, e.g., wherein both cartridge assembly 360 and anvil assembly 350 are pivotable relative to one another and proximal housing 340.

With continued reference to FIG. 5, and with additional reference to FIGS. 6-9, proximal housing 340 of distal tool assembly 330, as mentioned above, houses the distal portion 144 of drive assembly 140. More specifically, proximal housing 340 defines an internal cavity 342 that communicates at its proximal end with elongated fluid tube 146 and defines an open distal end. A piston base 344 is slidably disposed and sealingly engaged within open distal end of proximal housing 340 such that, as mentioned above, internal cavity 158 of piston-receiving member 150 (see FIGS. 3-4), internal passageway 147 of elongated fluid tube 146 (see FIG. 3-4), and internal cavity 342 of proximal housing 340 cooperate to define the cavity that is substantially filled with the pre-determined volume of actuating fluid "F," e.g., gas or liquid. Piston base 344 may be sealingly engaged within the open distal end of proximal housing 340 via an O-ring 345 or via any other suitable sealing engagement. Piston base 344 includes a distally-extending piston rack 346 that is configured to translate through elongated cavity 368 of cartridge assembly 360. Piston rack 346 includes a plurality of rack teeth 347 disposed along the length thereof. Teeth 347 extend downwardly from piston rack 346 and each defines a vertical, distally-facing surface 348, and an angled, proximally-facing surface 349. Distal portion 144 of drive assembly 140 further includes a biasing member 362, e.g., a spring, interdisposed between piston base 344 and cartridge assembly 360 and configured to bias piston base 344 proximally into internal cavity 342 of proximal housing 340.

Referring still to FIG. 5, anvil assembly 350 is pivotably engaged to proximal housing 340 of distal tool assembly 330 at the proximal end of anvil assembly 350 via a pivot pin 351. Pivot pin 351 may include a torsion spring (not shown) disposed thereabout. Alternatively, any other suitable biasing member may be disposed on or coupled to anvil assembly 350 for biasing anvil assembly 350 towards the open position relative to cartridge assembly 360. Anvil assembly 350 generally includes an anvil member 352 and an anvil cover 354. Anvil member 352 defines a fastener forming surface that generally opposes the tissue-contacting surface of cartridge assembly 360 when anvil assembly 350 is disposed in the closed position. The fastener forming surface of anvil member 352 may include a plurality of fastener pockets 356 configured to receive fasteners 400 and form fasteners 400 about tissue when fasteners 400 are driven from cartridge assembly 360 into fastener pockets 356 of anvil member 352. Anvil member 352 further includes an elongated vertically-oriented slot (not shown) that is configured to receive vertical support strut 372 of drive beam 370 and an elongated horizontally-oriented slot 359 that is configured to receive upper transverse bar 374 of drive beam 370, as will be described in greater detail below.

Cartridge assembly 360 of distal tool assembly 330 includes a base member 362 defining a tissue-contacting surface and a plurality of vertical slots (not shown) arranged in rows along the tissue-contacting surface thereof. Each vertical slot (not shown) is configured to house a fastener 400, such as a staple or clip, therein. A pusher 364 is disposed within each of the vertical slots (not shown) and is configured to abut the backspan of the respective fastener 400. Each pusher 364 defines a proximally-facing cam surface 365 that is configured to facilitate the upward urging of pushers 364 in response to longitudinal translation of drive sled 366 to eject fasteners 400 from cartridge assembly 360. Cartridge assembly 360 further includes an elongated, vertically-oriented central slot (not shown) that is configured to receive vertical support strut 372 of drive beam 370, and an elongated cavity 368 configured to slidably receive the distally-extending piston rack 346 of drive assembly 140 and slidably retain drive sled 366, as will be described in greater detail below. Drive sled 366 defines an angled distal surface 367 that is configured to contact proximally-facing cam surfaces 365 of pushers 364 upon translation through elongated cavity 368 of base member 362 of cartridge assembly 360 to facilitate the upward urging of pushers 364 to eject fasteners 400 from cartridge assembly 360.

Figure 6:
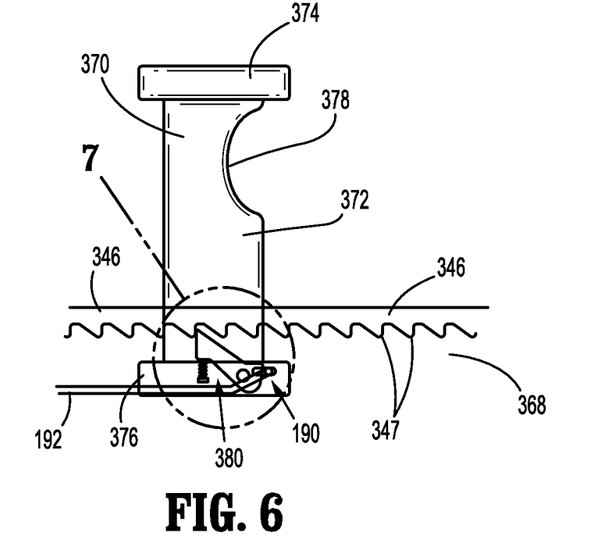
FIG. 6 is an enlarged, side view of the drive beam and rack and pawl system of the end effector assembly of FIG. 5.
Figure 7:
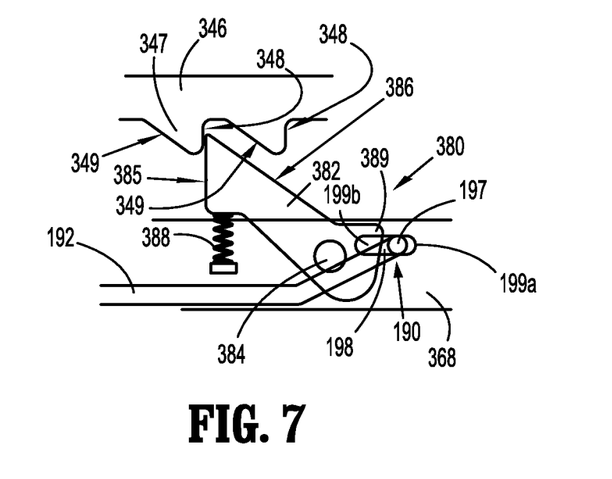
FIG. 7 is an enlarged view of the area of detail indicated as "7" in FIG. 6.

With reference to FIGS. 5-7, distal tool assembly 330 further includes a drive beam 370 that is selectively translatable through and relative to cartridge assembly 360 and anvil assembly 350 to pivot anvil assembly 350 to the closed position for clamping tissue between cartridge assembly 360 and anvil assembly 350; eject the plurality of fasteners 400 from cartridge assembly 360, through the clamped tissue, and into fastener pockets 356 to form fasteners 400 about tissue; and cut tissue clamped between cartridge assembly 360 and anvil assembly 350 between the rows of formed fasteners 400. Drive beam 370 includes a vertical support strut 372, an upper transverse bar 374 disposed at one end of vertical support strut 372, and a lower transverse bar 376 disposed at the opposite end of vertical support strut 372. Vertical support strut 372 is configured for translation through the elongated vertically-oriented slots (not shown) of anvil assembly 350 and cartridge assembly 360 and defines a cutting edge or knife 378 positioned to cut tissue clamped between anvil assembly 350 and cartridge assembly 360 upon translation therethrough. Upper transverse bar 374 is configured for translation through horizontally-oriented slot 359 of anvil assembly 350. Lower transverse bar 376 is configured for translation about the bottom, exterior surface of cartridge assembly 360.

Figure 8:
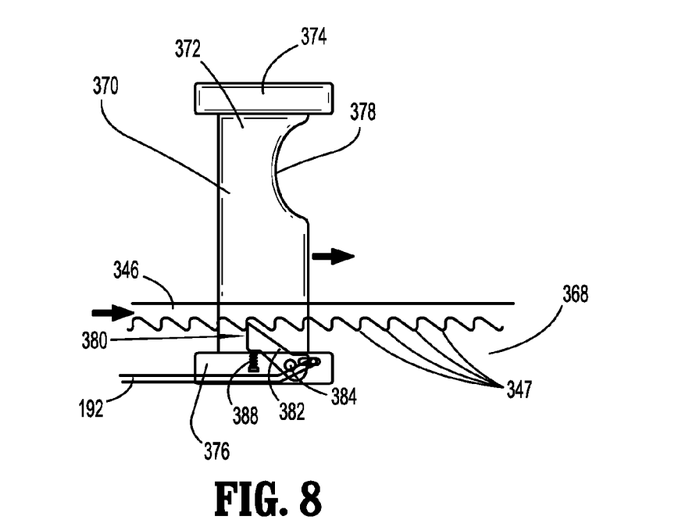
FIG. 8 is an enlarged, side view of the drive beam and rack and pawl system of FIG. 6 during advancement of the drive beam along the rack.
Figure 9:
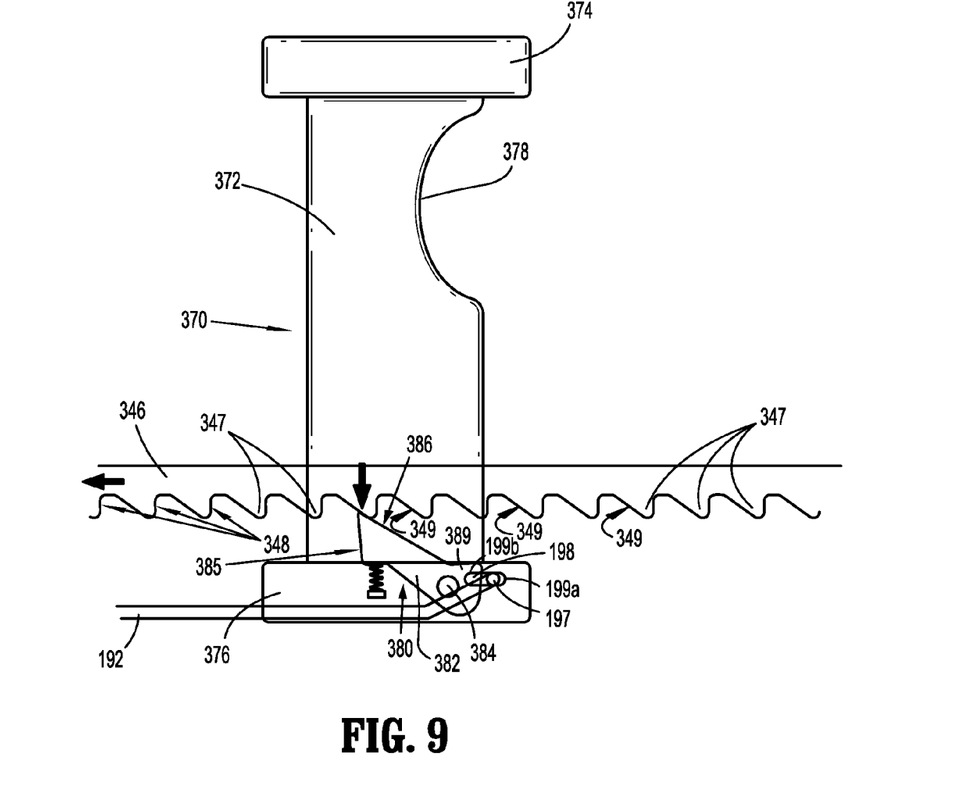
FIG. 9 is a greatly enlarged, side view of the drive beam and rack and pawl system of FIG. 6 during further advancement of the drive beam along the rack.

Continuing with reference to FIGS. 5-7, and with additional reference to FIGS. 8-9, drive beam 370 further includes a pawl assembly 380 and a retraction assembly 190 coupled towards the bottom end thereof, e.g., coupled to lower transverse bar 376. Pawl assembly 380 includes a pawl 382 that is pivotably coupled to drive beam 370 at a first end thereof via a pivot pin 384. The second, free end of pawl 382 defines a vertical engagement surface 385 and an angled engagement surface 386 that, as will be described below, facilitate the one-way advancement of drive beam 370 through cartridge assembly 360 to clamp, fasten, and/or cut tissue. Pawl assembly 380 further includes a biasing member 388, e.g., a spring, that is provided to bias the second, free end of pawl 382 in a generally upward direction into engagement with teeth 347 of piston rack 346.

With additional reference to FIG. 2, retraction assembly 190 includes a pin 197 slidably engaged within a longitudinal slot 198 defined within lower transverse bar 376 of drive beam 370 (or other suitable portion thereof). Retraction cord 192 is coupled to pin 197 and, as mentioned above, extends proximally through end effector assembly 300, elongated member 200, and cylindrical body portion 112 of housing 102 of motorized handle assembly 100, ultimately engaging retraction knob 196, which extends proximally from cylindrical body portion 112 of housing 102. In embodiments where end effector assembly 300 is releasably engagable with elongated member 200, retraction cord 192 may define proximal and distal sections that are releasably engagable with one another to permit releasable engagement of end effector assembly 300 and elongated member 200. Pin 197 is initially disposed at a distal end 199a of slot 198 such that pin 197 is spaced-apart from distal protrusion 389, which extends distally from the first end of pawl 382. As will be described below, upon retraction of retraction cord 192, e.g., via grasping and pulling retraction knob 196 proximally relative to housing 102, pin 197 is translated proximally through slot 198 towards the proximal end 199b thereof to urge the second, free end of pawl 382 to rotate downwardly out of engagement with distally-extending piston rack 346 of drive assembly 140 (FIGS. 3-4) and permit drive beam 370 to return proximally through cartridge assembly 360 back to its initial position.

Turning now to FIGS. 1-11, the operation of surgical fastener applying apparatus 10 for clamping, fastening, and cutting tissue is described. Initially, as shown in FIG. 5, drive beam 370 is disposed at the proximal end of cartridge assembly 360 and is positioned proximally of horizontally-oriented slot 359 defined within anvil assembly 350 such that anvil assembly 350 is disposed in the spaced-apart position relative to cartridge assembly 360. This position corresponds to the initial, unclamped, and un-actuated condition of surgical fastener applying apparatus 10. Further, in this initial, unclamped, un-actuated condition, as shown in FIGS. 3 and 5, piston 148 is biased proximally from piston-receiving member 150 under the bias of biasing member 152, piston base 344 is biased proximally into proximal housing 340, piston rack 346 is disposed in a more-proximal position within elongated cavity 368 of cartridge assembly 360, and drive sled 366 is disposed within elongated cavity 368 at the proximal end thereof. With surgical stapling apparatus 10 in this initial, unclamped, un-actuated condition, surgical fastener applying apparatus 10 may be maneuvered and/or manipulated into position, e.g., via actuating actuator button 104b (FIG. 1) to articulate end effector assembly 300 (see FIG. 2), such that tissue to be clamped, fastened, and/or cut is disposed between anvil assembly 350 and cartridge assembly 360.

With reference to FIGS. 3-4, in conjunction with FIGS. 1 and 5, once tissue to be clamped, fastened, and/or cut is disposed between anvil assembly 350 and cartridge assembly 360, end effector assembly 300 may be actuated. In order to actuate end effector assembly 300, one or more of actuator buttons 104a are actuated, e.g., depressed, to activate motor 122 which, in turn, drives drive axle 124 to rotate drive member 126. As drive member 126 is rotated by drive axle 124, first end 128 of drive member 126 contacts head 154 of piston 148 and urges body 156 of piston 148 distally into internal cavity 158 of piston-receiving member 150, against the bias of biasing member 152. Upon further rotation of drive member 126 by drive axle 124, second end 130 of drive member 126 is positioned adjacent piston 148, allowing piston 148 to return proximally under the bias of biasing member 152 such that body 156 is retracted proximally relative to internal cavity 158 of piston-receiving member 150. As can be appreciated, while motor 122 remains in an activated state, drive member 126 is repeatedly rotated by axle 124 such that piston 148 is repeatedly urged distally into piston-receiving member 150 and returned proximally, thus establishing a pulsed actuation configuration of drive assembly 140.

The distal advancement of piston 148 through piston-receiving member 150 upon each pulse of actuation of drive assembly 140 urges at least a portion of the pre-determined volume of fluid "F" substantially filling the cavity formed via internal cavity 158 of piston-receiving member 150, internal passageway 147 of elongated fluid tube 146, and internal cavity 342 of proximal housing 340, distally. Since the fluid "F" substantially fills the cavity, the distal urging of the fluid "F" via the insertion of piston body 156 further into piston-receiving member 150, creates sufficient pressure or force acting on piston base 344 so as to urge piston base 344 distally through proximal housing 340 against the bias of biasing member 162.

Referring now to FIGS. 5-8, as piston base 344 is urged distally through proximal housing 340 by the pneumatic or hydraulic (depending on whether the fluid "F" is a gas or liquid, respectively) pressure or force of the fluid "F" in each pulse, piston rack 346, which is engaged to and extends distally from piston base 344, is translated distally through elongated cavity 368 of cartridge assembly 360. As best shown in FIG. 8, as piston rack 346 is translated distally, drive beam 370 is likewise pushed distally due to the abutting engagement between the vertical, distally-facing surface 348 of one of the teeth 347 of piston rack 346 with the vertical engagement surface 385 of the second end of pawl 382. Distal translation of drive beam 370 through cartridge assembly 360, in turn, urges sled 366 distally. That is, each pulsed actuation of drive assembly 140 urges drive beam 370 and sled 366 distally through cartridge assembly 360 an incremental step distance. The cumulative effect of the incremental advancements of drive beam 370 and sled 366 upon repeated pulsed actuation of drive assembly 140 will be described in greater detail below.

With reference to FIGS. 3-5 and 9, as mentioned above, while motor 122 remains in an activated state, drive member 126 is repeatedly rotated by axle 124 such that piston 148 is repeatedly urged distally into piston-receiving member 150 by first end 128 of drive member 126 and returned proximally under the bias of biasing member 152, thus establishing the pulsed actuation of drive assembly 140. The distal translation of piston base 344 and piston rack 346 upon distal urging of piston 148 into piston-receiving member 150 to incrementally advance drive beam 370 and sled 366 through cartridge assembly 360 is described above. As mentioned above, as drive member 126 is rotated further such that second end 130 of drive member 126 is positioned adjacent piston 148, e.g., after a pulse of actuation of drive assembly 140, piston 148 is permitted to return proximally under the bias of biasing member 152. As piston 148 is returned proximally, the pressure or force of the fluid "F" no longer urges piston base 344 distally, thus allowing piston base 344 to return proximally under the bias of biasing member 162. The proximal return of piston base 344, in turn, pulls piston rack 346 proximally.

Referring to FIG. 9, as piston rack 346 is pulled proximally, teeth 347 of piston rack 346 are slid proximally past pawl 382. That is, although piston rack 346 is returned proximally, teeth 347 are slid proximally past pawl 382 such that drive beam 370 is retained in position relative to cartridge assembly 360. More specifically, as piston rack 346 is returned proximally, angled surfaces 349 of teeth 347 cam along angled engagement surface 386 of pawl 382 and urge the second, free end of pawl 382 downwardly against the bias of biasing member 388 to allow piston rack 346 to slide proximally relative to pawl 382. The frictional engagement of drive beam 370 within anvil assembly 350 and cartridge assembly 360 is sufficient to retain drive beam 370 in substantially fixed position upon proximal retraction of piston rack 346. Since drive beam 370 is maintained in position, sled 366 (FIG. 5), which is positioned distally adjacent drive beam 370, is likewise maintained in position during proximal retraction of piston rack 346.

Referring again to FIGS. 5-10, as can be appreciated, the above-described pawl and rack system provides for incremental advancement of drive beam 370 and sled 366 through cartridge assembly 360 upon each pulse of actuation of drive assembly 140. Repeated pulses of actuation of drive assembly 140, as described below, effect the sequential clamping of tissue between anvil assembly 350 and cartridge assembly 360, ejection of fasteners 400 from cartridge assembly 360 through tissue and into anvil assembly 350 for formation about tissue, and cutting of tissue between the rows of formed fasteners 400. Initially, drive beam 370 is disposed at the proximal end of cartridge assembly 360 and is positioned proximally of horizontally-oriented slot 359 defined within anvil assembly 350 such that pawl 382 is engaged with one of the proximally-disposed teeth 347 of piston rack 346. Sled 366 is initially disposed at the proximal end of cartridge assembly 360, distally adjacent drive beam 370. Upon each pulse of actuation of drive assembly 140, piston base 344 and piston rack 346 are urged distally such that drive beam 370 and sled 366 are likewise urged distally. Upon retraction of piston rack 346, pawl assembly 380 is slid along piston rack 346 until pawl 382 is engaged with a more-distally disposed tooth 347 of piston rack 346. Thus, with pawl 382 engaged with a more-distally disposed tooth 347 of piston rack 346, the above-described incremental advancement of drive beam 370 and sled 366 can be repeated to further advance drive beam 370 and sled 366, with pawl 382 engaging a more-distally disposed tooth 347 of piston rack 346 after each repetition. As such, drive beam 370 and sled 366 are advanced distally through cartridge assembly 360 and distally along piston rack 346 as piston rack 346 is repeatedly oscillated between proximal and distal positions by the pulsed activating of drive assembly 140 (FIGS. 3-5).

Referring to FIGS. 5 and 10, as drive beam 370 is initially advanced distally, vertical support strut 372 of drive beam 370 is advanced into the vertical slots (not shown) of anvil assembly 350 and cartridge assembly 360. Simultaneously or near-simultaneously therewith, upper transverse bar 374 of drive beam 372 enters horizontally-oriented slot 359 of anvil assembly 350 and lower transverse bar 376 of drive beam 372 is slidably disposed about the bottom exterior surface of cartridge assembly 360. Thus, as drive beam 370 is advanced distally, anvil assembly 350 is moved from the open position towards the closed position, e.g., anvil assembly 350 is approximated relative to cartridge assembly 360, to clamp tissue therebetween. Upon further distal advancement of drive beam 370, drive beam 370 is urged into contact with sled 366 to likewise urge sled 366 distally. As sled 366 is urged distally, angled surface 367 of sled 366 is sequentially urged into contact with angled surfaces 365 of pushers 364 to sequentially eject fasteners 400 from cartridge assembly 360, through tissue clamped between cartridge assembly 360 and anvil assembly 350, and into contact with anvil pockets 356 of anvil assembly 350 to form fasteners 400 about the clamped tissue. Knife 378, which is defined on vertical support strut 372 of drive beam 370, is positioned to follow slightly behind sled 366 to cut tissue between the rows of formed fasteners 400. As can be appreciated, actuation of drive assembly 140 (FIGS. 3-5) may be controlled to fire greater or fewer fasteners 400 from cartridge assembly 360, depending on a particular purpose. That is, drive beam 370 and sled 366 may be fully advanced through cartridge assembly 360, e.g., by fully depressing actuator button 104a (FIG. 1) or depressing actuator button 104a (FIG. 1) for a relatively longer period of time, to fire all of the fasteners 400 from cartridge assembly 360, or may only be actuated partially, e.g., by only partially depressing actuator button 104a (FIG. 1) or depressing actuator button 104a (FIG. 1) for a relatively shorter period of time, to fire only a portion of the plurality of fasteners 400 disposed within cartridge assembly 360.

Referring to FIGS. 1, 2, 10, and 11, once the desired firing operation is complete, drive beam 370 may be retracted back to its initial position to allow anvil assembly 350 to return to the spaced-apart position such that surgical fastener applying apparatus 10 may be removed from the surgical site. In order to retract drive beam 370, refraction knob 196 is pulled proximally relative to motorized handle assembly 100 such that retraction cord 192 is translated proximally through surgical fastener applying apparatus 10. As retraction cord 192 is translated proximally, pin 197 is translated proximally through slot 198 from the distal end 199a towards the proximal end 199b thereof. Upon proximal translation of pin 197 through slot 198, pin 197 ultimately contacts distal protrusion 389 of pawl 382 and urges distal protrusion 389 proximally such that the second, free end of pawl 382 is rotated downwardly against the bias of biasing member 388 and out of engagement with piston rack 346. With pawl 382 no longer engaged with teeth 347 of piston rack 346, retraction cord 192 may be pulled further proximally to translate drive beam 370 proximally through cartridge assembly 360 back to its initial position.

It will be understood that various modifications may be made to the embodiments of the surgical fastener applying apparatus disclosed herein. For example, the end effector assembly and motor assembly can be mechanically connected by pushers, rods, linkages or the like, in any of the embodiments disclosed herein. The end effector assembly may also be driven, in any of the embodiments disclosed herein, via manual power. In addition, the end effector assembly can be driven by a source of pressurized fluid, in the embodiments disclosed herein. Therefore, the above description should not be construed as limiting, but merely as exemplifications of embodiments. Those skilled in the art will envision other modifications within the scope and spirit of the present disclosure.

What is claimed is:

1. A surgical fastener applying apparatus, comprising:
    an end effector assembly including an anvil assembly and a cartridge assembly, at least one of the anvil assembly and the cartridge assembly movable relative to the other between an open position and a closed position for grasping tissue therebetween, the cartridge assembly configured to retain a plurality of surgical fasteners therein;
    a fluid-actuated drive assembly including a distal piston member configured to oscillate between a proximal position and a distal position, the distal piston member including a base and a rack extending distally from the base, the rack slidably disposed within the cartridge assembly;
    a drive beam configured for translation through the cartridge assembly to eject the plurality of surgical fasteners from the cartridge assembly; and
    a pawl assembly coupling the drive beam to the rack such that the drive beam is incrementally advanced along the rack and through the cartridge assembly as the distal piston member oscillates between the proximal position and the distal position.

2. The surgical fastener applying apparatus according to claim 1, wherein the fluid-actuated drive assembly includes a distal piston assembly including a piston housing, the distal piston member disposed within the piston housing, wherein fluid pressure within the piston housing urges the distal piston member to move from the proximal position to the distal position.

3. The surgical fastener applying apparatus according to claim 2, wherein the distal piston member is biased towards the proximal position such that, in the absence of fluid pressure within the piston housing, the distal piston member is returned from the distal position to the proximal position.

4. The surgical fastener applying apparatus according to claim 1, wherein the drive assembly further includes a proximal piston assembly and an elongated tube coupling the proximal piston assembly and the distal piston member, the elongated tube substantially filled with a fluid such that oscillation of the proximal piston assembly between first and second positions effects oscillation of distal piston member between the proximal and distal positions.

5. The surgical fastener applying apparatus according to claim 4, further comprising a motor assembly coupled to the proximal piston assembly and configured to drive the proximal piston assembly to oscillate between the first and second positions.

6. The surgical fastener applying apparatus according to claim 5, wherein the motor assembly includes an axle and a drive member eccentrically mounted about the axle, the motor configured to rotate the axle such that the drive member is rotated by the axle to drive the proximal piston assembly to oscillate between the first and second positions.

7. The surgical fastener applying apparatus according to claim 1, wherein the drive beam is further configured to engage the anvil assembly and the cartridge assembly upon distal translation of the drive beam to move the end effector assembly from the open position to the closed position.

8. The surgical fastener applying apparatus according to claim 1, wherein the pawl assembly is configured to engage the drive beam to the rack upon movement of the distal piston member from the proximal position to the distal position and wherein the pawl assembly is configured to disengage the drive beam from the rack upon movement of the distal piston member from the distal position back to the proximal position.

9. The surgical fastener applying apparatus according to claim 8, wherein the pawl assembly includes a pawl pivotably coupled to the drive beam, the pawl including a free end configured to engage a tooth of the rack upon movement of the distal piston member from the proximal position to the distal position and configured to slid about teeth of the rack upon movement of the distal piston member from the distal position back to the proximal position.

10. The surgical fastener applying apparatus according to claim 1, further comprising a retraction assembly coupled to the drive beam and the pawl assembly, the retraction assembly selectively actuatable for translating the drive beam proximally through the cartridge assembly.

11. The surgical fastener applying apparatus according to claim 10, wherein the retraction assembly include a retraction cord coupled to the drive beam and the pawl assembly at a first end thereof and having a retraction knob disposed at a second end thereof.

* * * * *